United States Patent [19]

Hall et al.

[11] Patent Number: 5,547,990
[45] Date of Patent: Aug. 20, 1996

[54] DISINFECTANTS AND SANITIZERS WITH REDUCED EYE IRRITATION POTENTIAL

[75] Inventors: Larry Hall, Nazareth, Pa.; Michael Y. Chiang, Flemington; Judith M. Meyer, Somerville, both of N.J.

[73] Assignee: Lonza, Inc., Fair Lawn, N.J.

[21] Appl. No.: 246,682

[22] Filed: May 20, 1994

[51] Int. Cl.$^6$ .......................... A61K 7/075; A61K 31/16; A61K 31/19; A61K 31/185

[52] U.S. Cl. .......................... 514/563; 424/70.1; 514/399; 514/401; 514/547; 514/549; 514/551; 514/562; 548/351.1; 548/352.1; 554/46; 554/47; 554/55; 554/59; 560/155; 560/170; 560/171; 562/105; 562/106; 562/567; 562/571

[58] Field of Search .......................... 424/70.1; 514/399, 514/401, 547, 549, 551, 562, 563; 548/351.1, 352.1; 554/46, 47, 55, 59; 560/155, 170, 171; 562/105, 106, 567, 571

[56] References Cited

U.S. PATENT DOCUMENTS

| | | | |
|---|---|---|---|
| 4,180,468 | 12/1979 | Tomidokoro et al. | 252/117 |
| 4,336,152 | 6/1983 | Like et al. | 252/106 |
| 4,652,585 | 3/1987 | Gerhardt et al. | 514/563 |
| 4,919,846 | 4/1990 | Nakama et al. | 252/542 |
| 4,931,216 | 6/1990 | Igarashi et al. | 252/547 |
| 5,211,883 | 5/1993 | Yamashina et al. | 252/546 |

OTHER PUBLICATIONS

Hall et al. "Disinfectants and Sanitizers–Global Issues 1992" given at CSMA/ADCS Detergent Industry Conference Sep. 13, 1992.

*Primary Examiner*—Peter O'Sullivan
*Attorney, Agent, or Firm*—Darby & Darby, P.C.

[57] ABSTRACT

It has been found that certain combinations of substituted imidazoline-based amphoterics and quaternary ammonium compounds show markedly reduced irritation profile in addition to providing excellent cleaning detergency. Moreover, it has further been found that certain substituted imidazoline amphoteric surfactants in combination with didecyl dimethyl ammonium chloride (DIDAC) show unexpected synergistic irritation reduction compared to that observed when the quaternary is an ADBAC type. This allows the formulation of disinfectants and sanitizers with the favored antimicrobial agent while at the same time affording the optimum reduction in irritation potential.

26 Claims, No Drawings

5,547,990

DISINFECTANTS AND SANITIZERS WITH REDUCED EYE IRRITATION POTENTIAL

BACKGROUND OF THE INVENTION

Sanitizers and disinfectants are formulations intended to reduce or destroy pathogenic bacteria, fungi and viruses. Quaternary ammonium compounds serve as the active antimicrobial agent in a wide variety of these formulations currently used in the household, industrial and institutional markets. They are effective at low concentrations and provide a broad spectrum of bactericidal activity, against both gram positive and gram negative bacteria. In addition to the antimicrobial agent, the formulations usually contain co-surfactants to assist in solubilizing soil particulates, as well as chelating agents to overcome deficiencies associated with hard water, and builders or acids to aid in cleaning performance. Over the years, these formulations have been optimized to afford excellent disinfection and sanitizing efficacy as well as providing good cleaning performance. As labor costs have been increasing substantially, there has been a trend toward the one-step disinfectant/cleaners. Modern formulations both clean and disinfect or sanitize in one application. This concept has also become attractive for the household market as well, where reducing cleaning time is desirable.

Unfortunately, standard quaternaries of choice, being cationic surfactants, are quite irritating to ocular tissue. This is especially so of dialkyl quaternary ammonium chlorides which are very efficient as a disinfectant. With increased concerns over pathogens in the household environment, the need for safe disinfectants and sanitizers has increased. Therefore, there is heightened interest in safe and mild household disinfectants and sanitizers and it is desirable to obtain a disinfectant formulation that is less irritating but still efficient as a disinfectant.

The co-surfactants used in most formulations also contribute to the overall irritation profile. The commonly used co-surfactants can be classified into two categories: nonyl phenol ethoxylates (NPE) and linear alcohol ethoxylates. Unfortunately, NPE's, especially those with the best detergency, exhibit high Draize eye scores and are appropriately labelled severely to moderately irritating. Linear alcohol ethoxylates are themselves less irritating, but do little to mitigate the irritation of the quaternary.

Several methods have been employed in the prior art to address the issue of reduced ocular irritation for disinfectant and sanitizer formulations. Unfortunately, none have combined a cost effective way to reduce irritation and enhance the overall cleaning performance of the formulation. Many co-surfactants, while lessening the irritation of the quaternary, impact negatively on the biocidal efficacy of the quaternary. While it is well known that anionic surfactants cannot be used in the presence of cationics, other surfactants including ethoxylates can dramatically reduce the biocidal efficacy of quaternaries (Futura, Taro, "Effect of Alkaline Builders and Surfactants on the Bactericidal Activity of Didecyldimethylammonium Chloride", *J. Antibac. Antifung. Agents* (1992) 20:12, pp. 617–22 (Japanese)).

An early patent, U.S. Pat. No. 3,402,242, assigned to Parachlor Chemical, describes the use of borax (sodium tetraborate) as an additive to a quaternary formulation being applied as a spray or in nebulized form. The borax was described as reducing the irritation to eyes, nose and throat of nebulized sprays in hospital rooms, nursing homes, etc. However, in a concentrate form, the borax would not be effective in reducing the irritation of the quaternary and would leave a residue upon application.

Today most of the use of quaternary disinfectants and sanitizers is in the area of dilutable concentrates, where a small amount of concentrate is diluted with water and then used to disinfect walls, floors, furniture, etc. or in the product category called RTU, or ready-to-use. RTU products contain the quaternary at use concentration and are a widely used type of disinfectant for the household market.

It has been recognized that at use dilution concentrations, e.g., 30–100 ppm, the irritability of quaternary ammonium compounds can be reduced by the addition of amphoteric surfactants and certain nonionic surfactants at 1:1 and 10:1 surfactant/quaternary ratios. "Disinfectants and Sanitizers—Global Issues 1992" presented by L. Hall, M. Chiang and D. Dutton of Lonza Inc. at CSMA/AOCS Detergent Industry Conference, Sep. 13, 1992. However, satisfactory techniques have not been found to mitigate the irritation of formulations having a high concentration of quaternary, particularly above the critical micelle concentration (CMC).

Two patents assigned to American Cyanamid address reducing the irritation of household disinfectants. In the first, U.S. Pat. No. 4,336,151, the invention describes the use of ethoxylated cocodiethanolamide, ethoxylated lanolin, hydrolyzed animal protein, allantoin, dextrose sugar and/or imidazole to mitigate the irritation of quaternaries. While the first two agents are effective at reducing ocular irritation, both are ethoxylates based on ethylene oxide, which have been shown to contain residual traces of 1,4-dioxane, a known carcinogen. Additionally, the protein, allantoin, dextrose sugar and imidazole, while all being effective at reducing ocular irritation of quaternary-based formulations, offer no other performance benefits. Indeed, residual sugar, for instance, unless totally and completely rinsed, leads to sticky residues, attracting ants and providing a food supply for microorganisms. Thus, while the formulations described do offer reduced ocular irritation, it does not come without drawbacks.

In U.S. Pat. No. 4,336,152, the use of maltodextrin as an irritation reducing compound for d-limonene containing disinfectants is described. The use of maltodextrin reduced the irritation profile from a Draize score of 74 to 2, a very substantial change in irritation potential. However, maltodextrin, like dextrose cited in U.S. Pat. No. 4,336,151, provides nothing in the way of cleaning enhancement or lower cost and can contribute to residue or other deposits.

In none of the aforementioned patents have all the critical objectives (i.e., low cost, enhanced cleaning performance, no post-application cleanup) been achieved. Therefore, there is a long standing need to provide a cost-effective, quaternary-based formulation that is both low in ocular irritation, while providing excellent in-use cleaning and detergency. Additionally, the formulation should provide one-step cleaning and disinfection and not require post-treatment rinsing nor cleanup in order to keep labor costs contained. Finally, it would be advantageous if the formulation could be based on readily available raw materials commonly used in detergent and cleaner manufacturing.

SUMMARY OF THE INVENTION

The present invention is based upon the unexpected discovery that the combination of (1) certain substituted imidazoline based amphoterics with (2) quaternary ammonium compounds produce concentrates that have reduced ocular irritation, exhibit efficient cleaning and wetting and, most importantly, are biocidally active. Surprisingly, the cleaning efficiency of the combination is superior to the cleaning efficiency of the quaternary compound alone. These products can be used as, but are not limited to, hard surface disinfectant cleaners and dips for workers in fields which require direct disinfecting of their hands. The concentrated formulations can also be used to make at use dilution products, such as RTUs.

Without intending to be bound to any theory, it is believed that the amphoteric surfactant is successful in reducing the irritation of the quaternary, above the critical micelle concentration, by incorporating the quaternary molecules into associative structures or micelles. By tightly binding the quaternary into these associative structures, the amphoteric structure reduces the cationic charge of the quaternary within the micelle, making the quaternary less irritating on contact with animal tissue. Upon subsequent dilution and below the critical micelle concentration (CMC), the quaternary exists dissociated from the surfactant and can perform unimpeded in its antimicrobial efficacy.

Furthermore, because many of the amphoteric surfactants exhibit two charged sites, one mole of surfactant can effectively reduce the irritation profile of two moles of quaternary, thereby making the amphoteric extremely cost effective.

DETAILED DESCRIPTION OF THE INVENTION

The quaternary ammonium compounds that can be used in the present invention include dialkyldimethylammonium chloride (DIDAC), alkyldimethylbenzyl ammonium chloride (ADBAC), alkyldimethylethylbenzyl ammonium chloride (ethylbenzyl quat), benzethonium chloride or any combinations of these compounds.

The general formula for the quaternary ammonium compound useful in the present invention has the following structure:

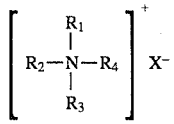

wherein $R_1$ and $R_2$ may be alkyl or alkoxy groups of 1 to 4 carbons; $R_3$ may be a straight or branched chain of 6 to 18 carbons; and $R_4$ may be either a straight or branched chain of 6 to 18 carbons, or a benzyl or alkylbenzyl, wherein the alkyl group may be of 2 to 8 carbons atoms.

Examples of DIDAC quaternary ammonium compounds that can be used in the present invention include dioctyldimethylammonium chloride, octyldecyldimethylammonium chloride, didecyldimethylammonium chloride, decylisononyldimethylammonium chloride, diisodecyldimethylammonium chloride, and combinations thereof.

Specific examples of ADBAC quaternary ammonium compounds for use in the present invention include alkyl ($C_{14}$ 50%, $C_{12}$ 40%, $C_{16}$ 10%) dimethylbenzyl ammonium chloride and alkyl ($C_{14}$ 60%, $C_{16}$ 30%, $C_{12}$ 5%, $C_{18}$ 5%) dimethylbenzyl ammonium chloride.

Commercially available imidazoline amphoteric surfactants can be used in the present invention and are generally synthesized by reacting a fatty acid with an amino ethyl ethanol amine to form an amide. Water is efficiently removed to form an imidazoline, which is then reacted with methyl acrylate and neutralized to produce the corresponding sodium salts.

The imidazoline amphoteric surfactants used in the present invention have the following general structure, according to the CTFA Cosmetic Ingredient Dictionary, Third Edition, published by the Cosmetic, Toiletry and Fragrance Association, Inc., Washington, D.C.:

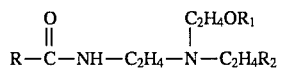

wherein R may be a fatty acid alkyl of 6 to 22 carbons; $R_1$ may be H or $C_2H_4COOH$ or $C_2H_4COONa$; $R_2$ may be COONa or

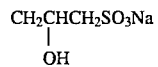

or $C_2H_4COONa$ or $CH_2COOCH_2COOH$ or $CH_2COOCH_2COONa$.

Specific examples of amphoteric surfactants that can be used in the present invention include sodium cocoamphoacetate, disodium cocoamphodiacetate, sodium cocoamphopropionate, and disodium cocoamphodipropionate.

These amphoteric surfactants can also be conventionally synthesized using well known methods and are produced by reacting methyl acrylate and alkylimidazoline at 1:1 to 2.5:1 ratios.

For use as a disinfectant, the quaternary ammonium compounds and amphoteric surfactants listed above can be blended in a weight ratio ranging about 10:1 to about 0.1:1 on a 100% active basis. Useful and preferred formulations in the present invention are listed in Table 1.

TABLE 1

| QUATERNARY/SURFACTANT (RATIO) | CONCENTRATE, % Active | | USE DILUTION PPM |
|---|---|---|---|
| | QUATERNARY | AMPHOTERIC | |
| Useful  10:1–0.1:1 | 0.25–25 | 0.1–30 | 10–10,000 |
| Preferred  5:1–0.3:1 | 0.5–10 | 0.3–10 | 100–1000 |

For use in a system with reduced ocular irritation, the quaternary ammonium compounds and amphoteric surfactants listed above can be blended in a molar ratio that ranges from 1:0.1 to 1:5, with the preferred range being 1:0.25 to 1:1. A blend of quaternary ammonium and amphoteric surfactant at these molar ratios result in an unexpected decrease in ocular irritation, even at high concentration of active quaternary (i.e., 10,000 ppm of active quaternary). Because quaternary ammonium compounds and amphoteric surfactants are aqueous solutions, any method for blending such solutions known in the art can be used. Cold mixing in a tank is a sufficient method.

The final formulations can also include chelators, builder salts, and dyes and fragrances such as those commonly used in the art in cleaning and disinfecting solutions. The percentage, by weight, of chelators that may be used in the final formulation ranges from 0.1 to 10 wt. %, with the preferred range being 0.5 to 5 wt. %. Examples of chelators that may be used are sodium and potassium salts of ethylenediaminetetraacetic acid (EDTA), citric acid, nitriloacetic acid, and various phosphoric acids and zeolites.

The percentage, by weight, of building salts that may be used in the final formulation ranges from 0.1 to 15 wt. %, with the preferred range being 0.1 to 0.5 wt. %. Examples of building salts that may be used include sodium metasilicate, sodium tripolyphosphate, sodium nitrilotriacetate, sodium carbonate, sodium silicate, citric acid salts and zeolites.

In addition, nonionic surfactants can be included in the final formulation. The percentage of these surfactants, by weight, in the final formulation may be from about 0.1 to 25 wt. % with a preferred range being 0 5 to 10 wt. %. When such nonionic surfactants are used at the use-dilution concentration, an unexpected synergistic effect with regard to cleaning efficiency is obtained. In such formulations where both nonionic and amphoteric surfactant are used along with the quaternary, less total surfactant, on an active weight percentage basis, is necessary to obtain a formulation with greater cleaning efficiency and less ocular irritation. Additionally, formulations comprising only the nonionic surfactant with the amphoteric surfactant, in a weight ratio of 0.1 to 10, are also part of the present invention.

Nonionic surfactants can be broadly defined as compounds produced by the condensation of a hydrophilic alkylene oxide group with an aliphatic or alkyl aromatic hydrophobic compound. Examples of preferred classes of nonionic surfactants are:

1. Long chain tertiary amine oxides corresponding to the following general formula:

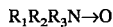

$$R_1R_2R_3N \rightarrow O$$

wherein $R_1$ contains an alkyl, alkenyl or monohydroxy alkyl radical of from about 8 to about 18 carbon atoms, up to about 10 ethylene oxide moieties, and up to 1 glyceryl moiety, and $R_2$ and $R_3$ contain from 1 to about 3 carbon atoms and up to about 1 hydroxy group, e.g., methyl, ethyl, propyl, hydroxyethyl, or hydroxypropyl radicals. Examples of amine oxides suitable for use in this invention include:
dimethyldodecylamine oxide,
oleyldi(2-hydroxyethyl)amine oxide,
dimethyloctylamine oxide,
dimethyldecylamine oxide,
dimethyltetradecylamine oxide,
di(2-hydroxyethyl)tetradecylamine oxide,
3-dodecoxy-2-hydroxypropyldi(3-hydroxypropyl)amine oxide, and dimethylhexadecylamine oxide.

2. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 6 to 60 moles of ethylene oxide per mole of alkyl phenol. The alkyl substituent in such compounds may be derived from polymerized propylene, diisobutylene, octane, or nonane.

3. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

4. The condensation product of straight or branched chain aliphatic alcohols having from 8 to 18 carbon atoms with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

The preferred surfactants to be used in the invention are nonyl phenol ethoxylates (6–12 moles), primary alcohol ethoxylates (3–12 moles), and secondary alcohol ethoxylates (3–12 moles).

Three criteria are used to test the formulations: microbial efficiency; ocular irritation potential; and cleaning efficiency. Tests for these three criteria are set forth below.

ANTIMICROBIAL EFFICIENCY

The effectiveness of the formulations of the invention in reducing and destroying pathogenic bacteria, fungi, or viruses is demonstrated by testing the various solutions against *Salmonella choleraesuis* and *Staphylococcus aureus* at 1:33 dilution rate, following the AOAC Use Dilution Test, a test protocol accepted by the EPA.

OCULAR IRRITATION

Ocular irritation is measured two ways, in vivo by the Draize and in vitro by the Bovine Corneal Opacity and Permeability Test ("BCOP").

Draize Rabbit Eye Test

Ocular irritation is measured by the Draize rabbit eye test, an acute eye irritation evaluation method currently accepted by the EPA (See *Principles and Procedures for Evaluating the Toxicity of Household Products,* National Academy of Science Publication 1138 (1977)). Three or six rabbits are used for each test. The test solution is administered to one eye of the rabbit. The other eye is used as a control. The eyes were compared at 1 hour, 1 day, 2 day, 3 day, 7 day, 14 day and 21 day timepoints, for the following three parameters: cornea opacity; damage to the iris; and damage to the conjunctiva.

Bovine Corneal Opacity and Permeability Test

The BCOP test (Gautheron, P. "Bovine Corneal Opacity and Permeability Test: an In Vitro Assay of Ocular Irritancy", *Fund. and Appl. Toxicol.* (1992) 18, pp. 442–49) is used to assess the ocular irritancy of the test materials to isolated bovine corneas. An in vitro score is determined based on the test material's induced opacity and permeability to fluorescein in the isolated bovine corneas.

The corneas of bovine eyes are excised and mounted in a corneal holder. They are exposed to 750 microliters of test materials then incubated for 10 minutes at 32° C., rinsed three times and incubated again for 2 hours. As the positive control, corneas are dosed with acetone, in the same fashion as with the test materials. An opacity measurement is performed on each cornea. The corrected opacity values for each treated cornea is calculated by subtracting the pre-treatment opacity readings from the post-treatment opacity readings. The mean opacity value of each cornea is calculated by averaging the corrected opacity values of the treated corneas for each treatment condition.

The BCOP assay is accepted when the positive control, acetone, causes an in vitro score that falls within two standard deviations of the historical mean. The following classification system is used to rank the BCOP scores:

| In Vitro Score | Classification |
| --- | --- |
| 0–25 | Mild irritant |
| over 25–55 | Moderate irritant |
| above 55.0 | Severe irritant |

CLEANING EFFICIENCY

Gardner Washability Test (ASTM #D4488-85)

The "Hard Surface Cleaning Using Pigment-Clay Soil" method is a test in which synthetic particulate and oily soil is applied to vinyl tiles and then the vinyl tiles are cleaned with detergent formulations using the Gardner Straight Line Washability Apparatus. The efficiency of soil removal is based on the color difference between soiled and washed tiles, which is measured by reflectance readings from a colorimeter. The result are expressed as percent soil removal (% SR).

The use of these formulations is also part of the present invention. It is contemplated that there would be many uses for a formulation with a quaternary concentration of 0.25 to 25 wt. %, which cause little or no irritation to ocular and other animal tissue. Such uses would include hard surface disinfectants/sanitizers, a hand dip for workers in such areas as the meat and poultry industry and the medical fields, antimicrobial handsoaps and sanitizing laundry rinses. These concentrated formulations can also be used as a starting material for other products, at use dilution, such as RTUs.

The following examples are illustrative of the present invention, however, it will be understood that the invention is not limited to the specific details set forth in the examples.

EXAMPLE 1

Formulations consisting of blends of DIDAC quaternary ammonium compounds and disodium cocoamphodipropionate (Amphoterge® K-2, a registered trademark of Lonza, Inc., Fair Lawn, N.J.) were tested by the in vitro BCOP method to rank ocular irritation. Quaternary ammonium compounds to surfactant molar ratios of 1:0.25, 1:0.5, and 1:1, at 10,000 ppm active quaternary, were evaluated.

TABLE 2

| % DIDAC, Active | % Surfactant, Active | Quaternary:Surfactant Molar | Quaternary:Surfactant Wt, Actives | In Vitro Toxicity BCOP Score | In Vitro Toxicity Irritation Rating |
| --- | --- | --- | --- | --- | --- |
| 1 | — | 1:0 | — | 89 | Severe |
| 1 | 0.33 | 1:0.25 | 1:0.33 | 58 | Moderate |
| 1 | 0.65 | 1:0.50 | 1:0.65 | 24 | Mild |
| 1 | 1.31 | 1:1 | 1:1.31 | 8 | Very Mild |

The quaternary to surfactant molar ratio of 1:0.25 was sufficient to reduce the in vitro ocular toxicity rating from a severe irritant to a moderate irritant. Unexpectedly, with 1:0.5 and 1:1 molar ratios of the DIDAC to the amphoteric surfactant, the in vitro ocular toxicity rating of the DIDAC is reduced to "mild irritant" and "very mild irritant."

EXAMPLE 2

The identical chemical formulations that were tested by BCOP in Example 1 were tested using the Draize test, and the results are in Table 3.

TABLE 3

| Quaternary:Surfactant | | In Vivo Toxicity Draize Score | | |
| --- | --- | --- | --- | --- |
| Molar | Wt, Actives | DAY 1 | DAY 7 | DAY 21 |
| 1:0 | — | 38 | 28 | 12 |
| 1:0.25 | 1:0.33 | 7 | 5 | 0.3 |
| 1:0.50 | 1:0.66 | 13 | 4 | 3.3 |
| 1:1 | 1:1.31 | 10 | 2 | 0 |

Similar to the BCOP scores, the one, seven and twenty-one day Draize scores all showed reduction in irritation by the DIDAC quaternary with the addition of the substituted imidazoline based amphoteric surfactant.

EXAMPLE 3

Formulations consisting of blends of ADBAC quaternary ammonium compounds and disodium cocoamphodipropionate were tested by the in vitro BCOP Test. The results are shown in Table 4. Formulations with quaternary ammonium compounds to surfactant molar ratios of 1:0, 1:0.5, and 1:1, in which there is 10,000 ppm (1%) active quaternary, were evaluated.

TABLE 4

| Quaternary:Surfactant | | In Vitro Toxicity | |
| --- | --- | --- | --- |
| Molar | Wt, Active | BCOP Score | Irritation Rating |
| 1:0 | — | 70 | Severe |
| 1:0.50 | 1:0.66 | 47 | Moderate |
| 1:1 | 1:1.32 | 42 | Moderate |

The BCOP scores for all of the formulations illustrate reduction in ocular irritation.

EXAMPLE 4

Several amphoteric surfactant types were blended with DIDAC at 1:0.5 quaternary to surfactant molar ratio and 10,000 ppm active quaternary. Ocular irritation was evaluated by the BCOP method. The amphoterics used were the following: sodium cocoamphopropionate, disodium cocoamphodipropionate, sodium cocoamphoacetate and disodium cocoamphodiacetate.

The results are summarized in Table 5.

TABLE 5

| % DIDAC, Active | Surfactant Type | Quaternary:Surfactant Molar | Quaternary:Surfactant Wt, Actives | In Vitro Toxicity BCOP Score | In Vitro Toxicity Irritation Rating |
| --- | --- | --- | --- | --- | --- |
| 1 | — | 1:0 | — | 89 | Severe |
| 1 | Sodium cocoamphopropionate | 1:0.5 | 1:0.53 | 32 | Moderate |
| 1 | disodium cocoamphodipropionate | 1:0.5 | 1:0.65 | 24 | Mild |
| 1 | sodium cocoamphoacetate | 1:0.5 | 1:0.51 | 59 | Severe |
| 1 | disodium cocoam- | 1:0.5 | 1:0.62 | 51 | Moderate |

TABLE 5-continued

| % DIDAC, Active | Surfactant Type | Quaternary:Surfactant Molar | Quaternary:Surfactant Wt, Actives | In Vitro Toxicity BCOP Score | In Vitro Toxicity Irritation Rating |
|---|---|---|---|---|---|
| | phodi-acetate | | | | |

As shown in the Table, each type of amphoteric surfactant reduced the quaternary from a severe irritant to a mild or moderate irritant at a ratio of 1:0.5 quaternary to surfactant, with disodium cocoamphodipropionate exhibiting the greatest irritation mitigation.

EXAMPLE 5

The imidazoline-based amphoteric surfactant can also be obtained by reacting different mole ratios of imidazoline to methyl acrylate (MAC) prior to the blending of the surfactant with the quaternary. The irritation mitigation effect of these surfactants on quaternary ammonium compounds were also investigated by the BCOP method.

TABLE 6

| % DIDAC, Active | Imidazoline/ MAC Ratio | Quaternary:Surfactant Molar | Quaternary:Surfactant Wt, Actives | In Vitro Toxicity BCOP Score | In Vitro Toxicity Irritation Rating |
|---|---|---|---|---|---|
| 1 | — | 1:0 | — | 89 | Severe |
| 1 | 1.3 | 1:0.5 | 1:0.57 | 62 | Severe |
| 1 | 1.6 | 1:0.5 | 1:0.60 | 43 | Moderate |
| 1 | 2.0 | 1:0.5 | 1:0.65 | 29 | Moderate |
| 1 | 2.5 | 1:0.5 | 1:0.67 | 28 | Moderate |

As shown in Table 6, a positive correlation between irritation mitigation effect and imidazoline to MAC ratio of the surfactant was established, with the higher the ratio, the greater the irritation reduction effect. In three out of four cases, the ocular irritation potential of the quaternary was reduced from severe to moderate by the addition of the surfactant.

EXAMPLE 6

Formulations of dialkyl dimethyl ammonium compound and amphoteric surfactant at various molar ratios, were tested against *Salmonella choleraesuis* (SC) and *Staphylococcus aureus* (SA), at a 1:33 dilution rate, by using AOAC Use Dilution Test.

The results are shown in Table 7.

TABLE 7

| Wt % DIDAC, Active | Wt % Amphoteric, Active | Quaternary:Surfactant Molar | Quaternary:Surfactant Wt, Actives | AOAC Use Dilution; deionized water S.C. ATCC #10708 | AOAC Use Dilution; deionized water S.A. ATCC #6538 |
|---|---|---|---|---|---|
| 1 | — | 1:0 | — | 0/20 | 0/20 |
| 1 | 0.33 | 1:0.25 | 1:0.33 | 0/20 | 0/20 |
| 1 | 0.65 | 1:0.50 | 1:0.65 | 0/20 | 0/20 |
| 1 | 1.31 | 1:1 | 1:1.31 | 0/20 | 0/20 |

As shown by the Tables 2 and 7, an optimum molar ratio of quaternary to surfactant, in terms of balancing irritancy reduction with microbial efficiency is 1:0.5.

EXAMPLE 7

As shown by the previous examples, formulations of the present invention can be expected to have reduced ocular irritation as well as good (i.e., strong) microbial efficacy. The following examples demonstrate the cleaning efficacy of formulated systems, as well as the reduced ocular irritation and microbial efficacy.

The results are shown in Table 8.

TABLE 8

| Component, Actives % | A | B | C | D | E | F |
|---|---|---|---|---|---|---|
| DIDAC | 1.9 | 1.9 | 1.9 | 1.9 | 1.9 | 1.9 |
| EDTA Na4 | 0.76 | 0.76 | 0.76 | 0.76 | 0.76 | 0.76 |
| Nonionic | 6.1+ | 6.1+ | 3.0+ | 3.0+ | 6.1* | 3.0* |
| Disodiumcocamphodipropionate | — | 1.24 | 1.24 | 2.48 | — | 1.24 |
| DI Water | | | q.s. to 100 | | | |
| Total Surfactant Active wt % | 6.1 | 7.34 | 4.24 | 5.48 | 6.1 | 4.24 |
| S/Q wt/wt | 3.2 | 3.9 | 2.2 | 2.9 | 3.2 | 2.2 |
| S/Q molar | 1.6 | 2.1 | 1.3 | 1.8 | 1.6 | 1.3 |
| Quat/Amphoterage wt/wt Ratio | — | 1:1.53 | 1:1.53 | 1:0.77 | — | 1:1.53 |
| Molar Ratio | 1:0 | 1:0.5 | 1:0.5 | 1:1 | 1:0 | 1:0.5 |
| BCOP Score | 88 | 45 | 56 | 44 | 59 | 48 |
| BCOP Rating | Severe | Moderate | Severe | Moderate | Severe | Moderate |
| Performance at 1:64 Dilution in D.I. Water, 300 ppm actives | | | | | | |
| Gardner Cleaning | 58 | 79 | 60 | 75 | 50 | 50 |

TABLE 8-continued

| Component, Actives % | A | B | C | D | E | F |
|---|---|---|---|---|---|---|
| (% SR) | | | | | | |
| Antimicrobial Efficacy at 1:64 Dilution | | | | | | |
| SA, DI & 5% Soil | 1/20 | 1/20 | 0/20 | 1/20 | 0/20 | 1/20 |
| SC, DI & 5% Soil | 1/20 | 1/20 | 1/20 | 0/20 | 0/20 | 0/20 |

⁺Tergitol 15-S-12
*Neodol 25-12

As shown by Table 8, the formulation without disodium cocoamphodipropionate (Formulation A) gave a BCOP score of 88, a severe irritation rating. The addition of disodium cocoamphodipropionate (Formulation B) decreased the BCOP score to 45, a moderate irritation rating. Unexpectedly, this formulation also showed an increase in Gardner Cleaning score of 58% SR to 79% SR with the same microbial efficiency.

Another surprising result is obtained from a formulation which contains approximately two parts nonionic surfactant and one part amphoteric surfactant (Formulation C). While the total surfactant activity weight percentage is 50% less than that in Formulation B, Formulation C still has a lower irritation score without a loss in cleaning ability or microbial efficiency. This shows a synergistic activity between the nonionic and amphoteric surfactants.

While several nonionic surfactants may be used to obtain the aforementioned irritation reduction combined with cleaning improvement, the desired combination consisted of secondary alcohol ethoxylate and disodium cocoamphodipropionate which gave the best balance of detergency and low irritancy scores.

We claim:

1. A sanitizing and disinfecting composition comprising:

a) a quaternary ammonium compound, having the following general formula:

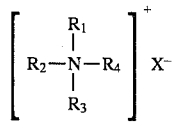

wherein $R_1$ and $R_2$ may be alkyl or alkoxy groups of 1 to 4 carbons; $R_3$ may be a straight or branched chain of 8 to 12 carbons; and $R_4$ may be either a straight or branched chain alkyl group of 8 to 12 carbons, or a benzyl or alkylbenzyl, wherein the alkyl group may be of 2 to 8 carbons atoms; and b) a substituted imidazoline based amphoteric having the following general formula;

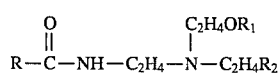

wherein R may be a fatty acid alkyl of 6 to 22 carbons; $R_1$ may be H or $C_2H_4COOH$ or $C_2H_4HCOONa$; $R_2$ may be COONa or

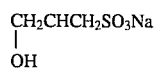

or $C_2H_4COONa$ or $CH_2COOCH_2COOH$ or $CH_2COOCH_2COONa$; wherein the concentration of said quaternary ammonium compound is about 0.25 to 25 wt. % and the concentration of said imidazoline amphoteric surfactant is about 0.1 to 30 wt. % and the weight ratio of said quaternary ammonium compound to said amphoteric surfactant is about 10:1 to 0.1:1.

2. The composition of claim 1, wherein said concentration of ammonium compound is about 0.5 to 10 wt. %.

3. The composition of claim 1, wherein said concentration of quaternary ammonium compound is greater than the critical micelle concentration.

4. The composition of claim 1, wherein said weight ratio is about 5:1 to 0.3:1.

5. The composition of claim 1, wherein the molar ratio of said quaternary ammonium compound to said amphoteric surfactant is about 1:0.1 to 1:5.

6. The composition of claim 5, wherein said molar ratio is about 1:0.25 to 1:1.

7. The composition of claim 1, wherein said quaternary ammonium compound is alkyldimethylbenzyl ammonium chloride, dialkyldimethylammonium chloride, alkyldimethylethylbenzyl ammonium chloride, benzethonium chloride or combinations thereof.

8. The composition of claim 7, wherein said dialklydimethyl ammonium chloride is dioctyldimethylammonium chloride, octyldecyldimethylammonium chloride, didecyldimethylammonium chloride, decylisononyldimethylammonium chloride, diisodecyldimethylammonium chloride or combinations thereof.

9. The composition of claim 1, wherein said imidazoline amphoteric surfactant is sodium cocoamphoacetate, disodium cocoamphodiacetate, sodium cocoamphopropionate or disodium cocoamphodipropionate.

10. The composition of claim 1, wherein said composition further comprises one or more of the following: chelators; builder salts; dyes; fragrances; and nonionic surfactants.

11. The composition of claim 10, wherein the percentage of said chelator is about 0.1 to 10 wt. %.

12. The composition of claim 11, wherein the percentage of said chelator is about 0.5 to 5 wt. %.

13. The composition of claim 10, wherein said chelator is sodium or potassium salts of EDTA, citric acid, nitriloacetic acid, phosphoric acid or zeolite.

14. The composition of claim 10, wherein the percentage of said builder salt is 0.1 to 15 wt. %.

15. The composition of claim 14, wherein the percentage of said builder salt is 0.5 to 5 wt. %.

16. The composition of claim 10, wherein said builder salt is sodium metasilicate, sodium tripolyphosphate, sodium nitriloacetate, sodium carbonate, sodium silicate, citric acid salt or zeolite.

17. The composition of claim 10, wherein the percentage of said nonionic surfactant is 0.1 to 25 wt. %.

18. The composition of claim 17, wherein the percentage of said nonionic surfactant is 0.5 to 10 wt. %.

19. The composition of claim 10, wherein said nonionic surfactant is a long chain tertiary amine oxide; a polyethylene oxide condensate of alkyl phenols; a condensation product of ethylene oxide or ethylene oxide and propylene oxide; or a condensation product of alkylene oxides with straight or branched chain aliphatic alcohols.

20. A method of disinfecting and sanitizing comprising contacting animal skin with a composition of quaternary ammonium compound, having the following general formula:

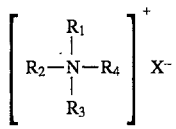

wherein $R_1$ and $R_2$ may be alkyl or alkoxy groups of 1 to 4 carbons; $R_3$ may be a straight or branched chain of 8 to 12 carbons; and $R_4$ may be either a straight or branched chain alkyl group of 8 to 12 carbons, or a benzyl or alkylbenzyl, wherein the alkyl group may be of 2 to 8 carbons atoms and a substituted imidazoline based amphoteric having the following general formula:

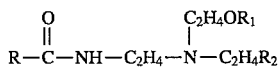

wherein R may be a fatty acid alkyl of 6 to 22 carbons; $R_1$ may be H or $C_2H_4COOH$ or $C_2H_4COONa$; $R_2$ may be COONa or

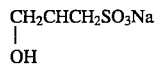

or $C_2H_4COOHa$ or $CH_2COOCH_2COOH$ or $C_2H_4COOCH_2COONa$, wherein the concentration of said quaternary ammonium compound is about 0.25 to 25 wt. % and the concentration of said amphoteric is about 0.1 to 30 wt. % and the weight ratio of said quaternary ammonium compound to said amphoteric surfactant is about 10:1 to 0.1:1.

21. The method of claim 20, wherein said concentration of said quaternary is about 0.5 to 10 wt. %.

22. The method of claim 20, wherein said concentration of said active quaternary ammonium compound is greater than the critical micelle concentration.

23. The method of claim 20, wherein said animal skin is human.

24. A method of sanitizing and disinfecting comprising contacting a hard surface with a formulation of quaternary ammonium compound, having the following general formula:

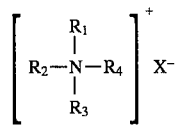

wherein $R_1$ and $R_2$ may be alkyl or alkoxy groups of 1 to 4 carbons; $R_3$ may be a straight or branched chain of 8 to 12 carbons; and $R_4$ may be either a straight or branched chain alkyl group of 8 to 12 carbons, or a benzyl or alkylbenzyl, wherein the alkyl group may be of 2 to 8 carbons atoms and a substituted imidazoline based amphoteric having the following general formula:

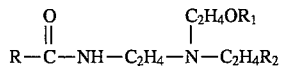

wherein R may be a fatty acid alkyl of 6 to 22 carbons; $R_1$ may be H or $C_2H_4COOH$ or $C_2H_4COONa$; $R_2$ may be COONa or

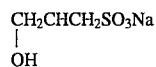

or $C_2H_4COONa$ or $CH_2COOCH_2COOH$ or $C_2COOCH_2COONa$, wherein the concentration of said quaternary ammonium compound is about 0.25 to 25 wt. % and the concentration of said amphoteric is about 0.1 to 30 wt. % and the weight ratio of said quaternary ammonium compound to said amphoteric surfactant is about 10;1 to 0.1:1.

25. The method of claim 24, wherein said concentration of said quaternary ammonium compound is about 0.5 to 10 wt. %.

26. A method of making a sanitizing and disinfecting composition comprising adding to a formulation of quaternary ammonium having the following general formula:

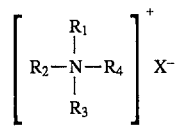

wherein $R_1$ and $R_2$ may be alkyl or alkoxy groups of 1 to 4 carbons; $R_3$ may be a straight or branched chain of 8 to 12 carbons; and $R_4$ may be either a straight or branched chain alkyl group of 8 to 12 carbons, or a benzyl or alkylbenzyl, wherein the alkyl group may be of 2 to 8 carbons atoms and substituted imidazoline based amphoteric having the following general formula:

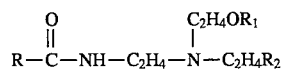

wherein R may be a fatty acid alkyl of 6 to 22 carbons; $R_1$ may be H or $C_2H_4COOH$ or $C_2H_4COONa$; $R_2$ may be COONa or

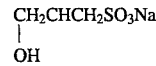

or $C_2H_4HCOONa$ or $CH_2COOCH_2COOH$ or $CH_2COOCH_2COONa$, wherein the concentration of said quaternary ammonium compound is above 0.25 wt. %, an amount of water sufficient to reduce the concentration of said quaternary ammonium compound to below 0.25 wt. % and the weight ratio of said quaternary ammonium compound to said amphoteric surfactant is about 10:1 to 0.1:1.

* * * * *